United States Patent [19]

Songer

[11] Patent Number: 5,611,801
[45] Date of Patent: Mar. 18, 1997

[54] METHOD AND APPARATUS FOR BONE FRACTURE FIXATION

[75] Inventor: Matthew N. Songer, Marquette, Mich.

[73] Assignee: Pioneer Laboratories, Inc., Marquette, Mich.

[21] Appl. No.: 346,152

[22] Filed: Nov. 29, 1994

[51] Int. Cl.⁶ .................................................. A61B 17/82
[52] U.S. Cl. ............................ 606/73; 606/74; 606/103; 606/104
[58] Field of Search ......................... 606/103, 74, 73, 606/75, 232, 104, 105, 226, 72

[56] References Cited

U.S. PATENT DOCUMENTS

| | | | |
|---|---|---|---|
| 2,411,079 | 11/1946 | Baule | 606/226 |
| 2,501,978 | 3/1950 | Wichman . | |
| 4,041,939 | 8/1977 | Hall . | |
| 4,632,100 | 12/1986 | Somers et al. . | |
| 4,643,178 | 2/1987 | Nastari et al. | 606/103 |
| 4,790,303 | 12/1988 | Steffee . | |
| 5,037,426 | 8/1991 | Goble et al. . | |
| 5,071,420 | 12/1991 | Paulos et al. . | |
| 5,129,902 | 7/1992 | Goble et al. . | |
| 5,141,520 | 8/1992 | Goble et al. | 606/232 |
| 5,152,790 | 10/1992 | Rosenberg et al. . | |
| 5,156,616 | 10/1992 | Meadows et al. . | |
| 5,318,566 | 6/1994 | Miller . | |
| 5,474,554 | 12/1995 | Ku | 606/74 |

Primary Examiner—Guy V. Tucker
Attorney, Agent, or Firm—Gertsman, Ellis & McMillin, Ltd.

[57] ABSTRACT

Fixation of a bone fracture may be accomplished by screw driving a threaded pin into the bone, typically in a manner to cause the pin to advance across the fracture area of the bone. It is also common for a pair or more of said pins to be driven into the bone in the manner described above. The threaded pin or pins each may have a cable secured to the pin, extending outwardly from the proximal pin end. One then wraps the cable or cables around the bone to provide external securance for fixation of the bone fracture. A pair of cables used in this process may be secured together under tension by a crimp. Otherwise, a single, free cable end may be secured to a separate pin or other anchor as desired.

14 Claims, 1 Drawing Sheet

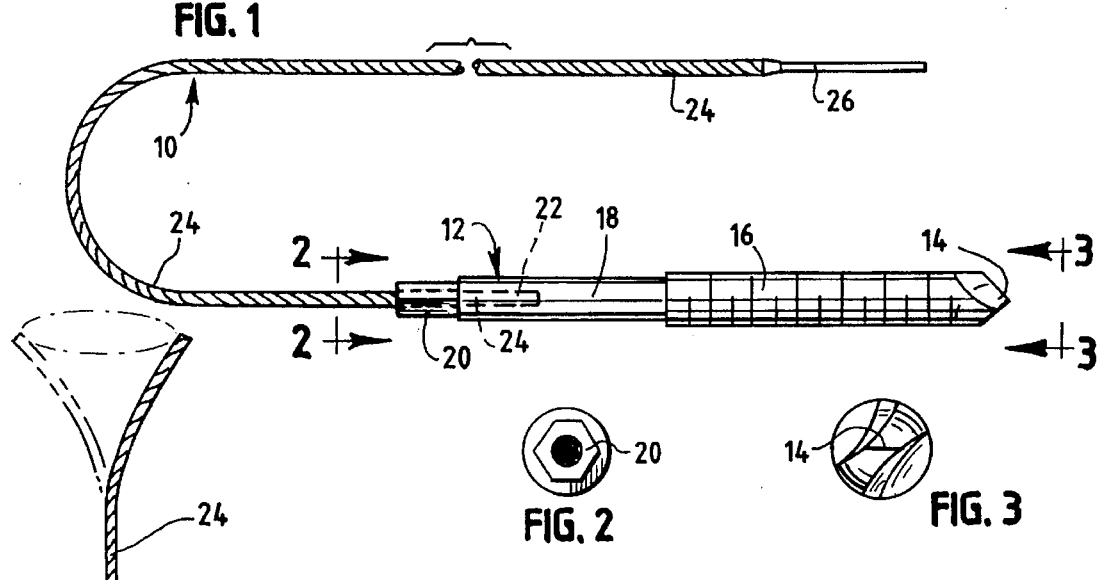
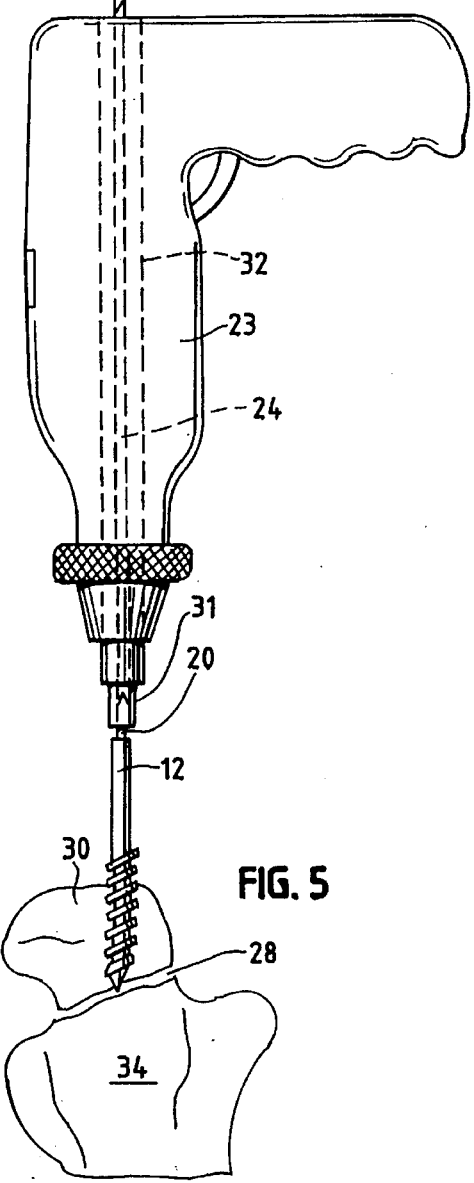
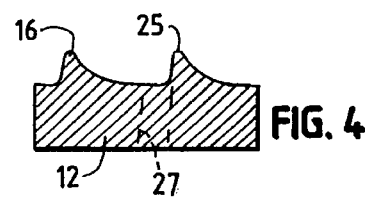
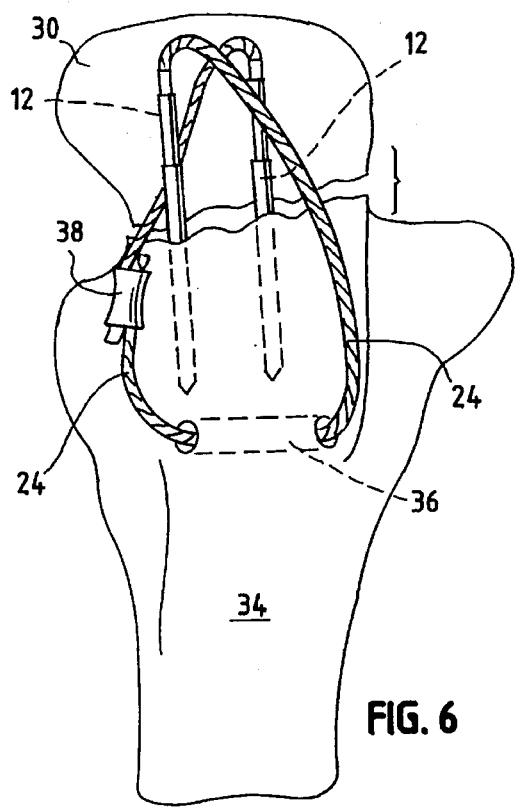

METHOD AND APPARATUS FOR BONE FRACTURE FIXATION

BACKGROUND OF THE INVENTION

Certain types of fractures of bones cannot be effectively healed without the use of a bone screw, a bone pin, a cable, or a cerclage wire, the use of all of which is known to the prior art. Also, it is been known to use a screw or a pin in combination with a cable or a cerclage wire in an attempt to provide both internal securance and external securance of a fractured bone. However, as a continuing problem, bone screws can slowly unscrew due to the normal motions of a patient during and after convalescence. This of course can cause serious problems and may require further surgery.

On the other hand, cable wrappings can slip out of their optimum position on a bone and thus lose some of their benefit.

In accordance with this invention, a bone fracture may be both internally and externally fixed, while avoiding the above described disadvantages which are found in the use of separate, threaded pins and separate cables in the fixation of bone fractures.

DESCRIPTION OF THE INVENTION

By this invention, a bone fracture may be fixated by the steps of: screw driving a threaded pin into the bone. In most cases it is desirable to cause the threaded pin to advance across the fracture area of the bone, i.e. the line of fracture, to provide internal securance for fixation of the bone fracture by the holding action which is provided by the threaded pin to the two pieces of bone separated by the fracture. By this invention, the threaded pin has a cable which is secured to the pin in typically a permanent manner, so that it cannot be separated without destroying the device. The cable extends outwardly from the proximal pin end. One then wraps the cable around the bone, typically after driving of the pin, to provide external securance for fixation of the bone fracture.

Thus, external securance and internal securance can be provided by the same fixation device. Also, added advantages are provided above and beyond the separate use of a bone pin and a separate cable, in that the tension which is applied to the threaded pin by the attached cable, and the very attachment of the cable itself, substantially prevents the unplanned unscrewing of the threaded pin after it has been implanted due to movements of the patient. At the same time, the threaded pin provides a solid anchor for the cable, so that disadvantages found in the two separate items are eliminated.

It is often desirable to screwdrive a pair of threaded pins into the bone in spaced relationship to each other, with each of the threaded pins having a cable which is secured to the pin and extending outwardly from each proximal pin end. One then wraps the bone with the cables to promote external fixation of the bone fracture, and one secures the cable ends together, typically under tension and with the use of a conventional crimp.

Here also, it is typically desirable for at least one and preferably both of the threaded pins to cross the fracture surface, to provide internal securance for fixation of the bone fracture, along with the external securance that is provided by the cables which are attached to the pins and typically are secured together after pin implantation. Preferably, a driver fitting, such as a polygonal driver member, may be carried on the proximal pin end (which is opposite to the driving point of the pin). This driver fitting may be engaged with a pin driver, preferably a pin driver in which the cable of the pin extends centrally through the pin driver, as the pin driver advances the pin into the bone. With such an arrangement, the pin driver rotates the pin and advances it until the proximal or rear end of the pin is preferably substantially flush with the surface of the bone, or even recessed. Because the tension of the cable prevents retraction of the screw threaded pin over the long term, there is no need for a retention head or the like pressing against an outer surface of the bone to prevent such undesired screw-thread rotation.

The cable pin of this invention may be used to secure fractured surfaces of bones together in a variety of situations, including the following fractures: olecranon fractures, patellar fractures, proximal humerus fractures, greater trochanteric fractures, greater tuberosity humerus fractures, femur fractures, medial malleolus tibial fractures, and calcaneus fractures, among others.

Thus, the use of a cable secured to a pin and under tension provides a double advantage: it provides the external support for a bone fracture that is needed in many instances, but it also serves to prevent unplanned withdrawal of the threaded bone pin without the need for any retention structures outside of the bone. At the same time, the bone pin serves as a solid anchor for the cable, restricting and reducing undesired slippage of the cable.

DESCRIPTION OF THE DRAWINGS

In the drawings FIG. 1 is a plan view of a bone fixation device in accordance with this invention;

FIG. 2 is a sectional view taken along line 2—2 of FIG. 1;

FIG. 3 is an end view taken along line 3—3 of FIG. 1;

FIG. 4 is an enlarged, fragmentary, transverse section showing the shape of cancellous threads, which may be the design of threads used in the pin of FIG. 1;

FIG. 5 is a perspective view showing the installation of a bone pin through a fracture surface of a bone which has suffered an olecranon fracture; and FIG. 6 shows a subsequent step in the process of FIG. 5, with two implanted bone pins having their cables wrapped about the fractured bone and crimped together at their ends.

DESCRIPTION OF SPECIFIC EMBODIMENTS

Referring to FIGS. 1 through 4, the cable-carrying pin of this invention 10 is shown. Pin 12 is made of solid metal, typically of a body implantable alloy such as 316 L stainless steel, ASTM F-138-86; titanium alloy 6 AL-4V, ASTM F-136-92; or cobalt chrome alloy, ASTM F-90, among others. Pin 12 defines a self-tapping point 14 at one end, plus cancellous threads 16, which point and threads may be of generally conventional design for a surgical threaded pin.

The threads 16 extend about half the entire distance of pin 12, with a proximal or rear portion of pin 18 being cylindrical in shape and of less outer diameter than the threads 16, as shown. At the proximal end of pin 12, an external, hexagonal driver fitting 20 is provided, to fit with a cannulated power drill 22 for driving as illustrated in FIG. 5. Alternatively, a manual brace and bit may be used for driving the threaded pin 12 as well.

Pin 12 defines a lumen 22 extending inwardly from its proximal end a short distance, typically less than half the length of pin 12. A multi-strand wire cable 24 occupies lumen 22 and is secured therein by adhesive or by welding of some form, for example resistance welding, for a permanent attachment of an end of cable 24 to pin 12. Cable 24 may be of generally conventional design for surgical use, having a diameter of 0.04 to 0.05 inch, for example. The metals used for the multiple strand cable may be similar to the metals used to manufacture pin 12. Also, cobalt chrome, ASTM F-1091-91 may be used or titanium 6AL-4V, ASTM F-136-84.

Solid wire leader 26 is welded or otherwise permanently adhered to the end of cable 24 which is opposed to pin 12. Wire leader 26 may have a diameter of about 1 mm., typically less than the diameter of the cable, being used to facilitate the placement of the cable around the bone, making easier the penetration of the cable through narrow spaces and the like, rather in the manner of the solid end tip of a shoelace. After installation, the leader 26 and a portion of the cable 24 are typically cut away.

Pin 12 will preferably conform to ASTM standard F-543-92, entitled *Standard Specifications for Cortical Bone Screws* with respect to materials, threads, finish, and identification. The pin 12 may specifically have a length of 20 to 75 mm. Its larger diameter 25 of the screw threads may range from 3.5 mm. to 4.5 mm., while the minimum diameter 27 of pin 18 at the threaded portion may be 2.5 mm. to 3.5 mm. The pin tip 14 may be in the form of a diamond point, a chisel point, a trochar point, or the like.

The method of this application is illustrated in FIGS. 5 and 6. In FIG. 5, an olecranon fracture at fracture area 28 is presented. It can be seen that the relatively small bone tip 30 which has broken off with the fracture is going to be set only with substantial difficulty, since the small bone piece 30 will tend to be very mobile.

Bone pin 12 is mounted in the cannulated power drill 23, with hexagonal driver fitting 20 of the pin fitting in a female hexagonal chuck 31 or the like of power drill 23 in conventional manner. Cable 24 typically extends through the length of power drill 23 within a bore 32 so as to be out of the way and to avoid crimping of the cable. Such cannulated power drills are generally known to the art.

Then, pin 12 is driven through the bone, beginning with the small fractured portion 30, crossing fracture area 28, with all threads being spaced from area 28. Pin 12 enters deeply into the main portion 34 of the bone, so that all of pin 12 is typically sunk into the bone, with hexagonal drive fitting 20 being flush with the bone surface or even recessed. Clinical advantages are achieved through the absence of a projecting outer portion of the bone pin, without the need for a locking plate or the like to prevent back rotation of the bone pin.

FIG. 6 shows a particular surgical procedure for use of a pair of bone pins in accordance with this invention. It is to be understood that the bone pins of this invention may be used in a wide variety of surgical procedures, and not just the particular one illustrated.

As shown in FIG. 6, a pair of bone pins 12 are driven through bone portion 30, fracture area 28, and bone 34 as illustrated in FIG. 5, to provide internal securance of the fractured bone portion 30 to the rest of the bone 34. The respective cables 24 of the bone pins are then secured in the manner illustrated in FIG. 6 to provide external support of the olecranon fracture, with one of the cables 24 being shown to pass through a surgically created tunnel 36, and to then enter into engagement with the other cable 24. The cables are placed under tension, and then secured together with a tubular crimp 38 or the like in a manner which is generally conventional.

Thus, a fractured bone may be secured together, with internal securance provided by pins 12 and external securance provided by cable 24 for improved securance of difficult fractures. Back-rotation of threaded pins 12 is prevented because of their connection with the tensioned cables 24. On the other hand the cables 24 are provided with a strong and solid anchor relative to the bone to minimize cable slippage.

The above has been offered for illustrative purposes only, and is not intended to limit the scope of the invention of this application, which is as defined in the claims below.

That which is claimed is:

1. The method of fixation of a bone fracture, which comprises:

screw driving a pair of threaded pins into said bone in spaced relationship, each of said threaded pins having a cable secured to said pin and extending outwardly from the proximal pin end to a free cable end; wrapping said bone with said cables to promote fixation of said bone fracture; and securing said cable ends together.

2. The method of claim 1 in which at least one of said threaded pins crosses the fracture area to provide internal securance for fixation of said bone fracture.

3. The method of claim 1 in which the proximal pin end carries a drive fitting that permits said pin to be essentially completely advanced into said bone.

4. The method of claim 1 in which the cable of each pin extends centrally through a pin driver as the pin driver advances each pin into the bone.

5. The method of fixation of a bone fracture, which comprises:

screw driving a threaded pin into said bone in a manner to cause said pin to advance across the fracture area of the bone, to provide internal securance for fixation of said bone fracture; said threaded pin having a cable secured to said pin and extending outwardly from the proximal pin end; and wrapping said cable around said bone to provide external securance for fixation of said bone fracture.

6. The method of claim 5 in which the proximal pin end carries a drive fitting that permits said pin to be essentially completely advanced into said bone.

7. The method of claim 6 in which the cable of each pin extends centrally through a pin driver as the pin driver advances each pin into the bone.

8. The method of claim 5 in which the cable of each pin extends centrally through a pin driver as the pin driver advances each pin into the bone.

9. A device for fixation of bone fractures, which comprises: a pin defining a bone penetrating point at one end thereof and screw threads defined on said pin adjacent said point; a multistrand cable attached to said pin and extending from the end of said pin opposite said one end outwardly therefrom to an outer cable end; a polygonal driver member carried on said opposite pin end and surrounding said cable, to engage a rotary pin driver, said pin being solid and lumen-free along the majority of its length.

10. The fixation device of claim 9 having a wire leader attached to said outer cable end.

11. The fixation device of claim 10 in which said multistrand cable is made of metal.

12. The fixation device of claim 9 in which said cable is attached to said opposite pin end.

13. The method of fixation of a bone fracture, which comprises:

screw driving a threaded pin into said bone in a manner to cause said pin to advance across the fracture area of the bone, to provide internal securance for fixation of said bone fracture, and threaded pin having a cable secured to said pin and extending outwardly from the proximal pin end; and wrapping said cable around said bone to provide external securance for fixation of said bone fracture, said pin being completely advanced into said bone during said driving into the bone, said cable extending centrally through a pin driver as the pin driver advances said pin into the bone.

14. The method of claim 13 in which a pair of threaded pins are driven into said bone in spaced relationship, and including the step of wrapping said bone with said cables which extend outwardly from said proximal pin ends to promote fixation of said bone fracture; and securing said cable ends together.

* * * * *